United States Patent [19]

Shionozaki et al.

[11] Patent Number: 4,723,018
[45] Date of Patent: Feb. 2, 1988

[54] 2-PHENYLPYRIDINE DERIVATIVES

[75] Inventors: Yoshio Shionozaki; Hiroshi Mukai; Tsuyoshi Obikawa; Shuhei Yamada; Rei Miyazaki, all of Nagano, Japan

[73] Assignee: Seiko Epson Corporation, Tokyo, Japan

[21] Appl. No.: 5,798

[22] Filed: Jan. 21, 1987

[30] Foreign Application Priority Data

Jan. 27, 1986 [JP] Japan .................................. 61-15237
Apr. 16, 1986 [JP] Japan .................................. 61-87633
May 1, 1986 [JP] Japan .................................. 61-101354
May 1, 1986 [JP] Japan .................................. 61-101355
May 1, 1986 [JP] Japan .................................. 61-101356

[51] Int. Cl.$^4$ ............................................. C07D 213/30
[52] U.S. Cl. ...................................... 546/342; 546/339
[58] Field of Search .............................. 546/339, 342

[56] References Cited

U.S. PATENT DOCUMENTS 4,579,850 4/1986 Wong ................................... 546/342

Primary Examiner—Henry R. Jiles
Assistant Examiner—J. Richter
Attorney, Agent, or Firm—Blum Kaplan

[57] ABSTRACT 2-phenylpyridine derivatives having the general formula:

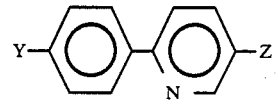

wherein Y is

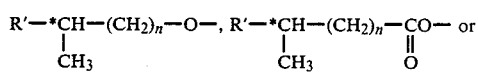

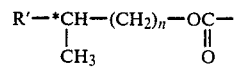

and Z is a straight chain alkyl group having from 1 to 16 carbon atoms,

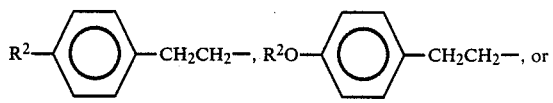

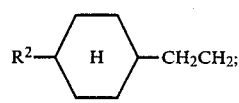

R' is a straight chain alkyl group having from 2 to 12 carbon atoms, R$^2$ is a straight chain alkyl group having from 1 to 12 carbon atoms, n is an integer from 1 to 10 and * is an asymmetric carbon are provided. The derivatives are stable, have low viscosity, excellent electro-optical response properties and broaden the ferroelectric temperature range when added to ferroelectric liquid crystal compositions.

9 Claims, 2 Drawing Figures

2-PHENYLPYRIDINE DERIVATIVES

BACKGROUND OF THE INVENTION

This invention relates generally to 2-phenylpyridine derivatives, and more particularly, to ferroelectric liquid crystal materials including the 2-phenylpyridine derivatives that are useful in ferroelectric liquid crystal display devices.

Ferroelectric liquid crystal materials have recently attracted attention due to their high response speed and good memory properties as discussed in N. A. Clark et al, *Applied Physics Letters,* Vol. 36, p. 899 (1980). Similar properties are not obtainable using prior art liquid crystal materials. In recent years investigators have sought practical uses for such ferroelectric liquid crystal materials. Accordingly, there is a need to develop ferroelectric liquid crystal materials that are suitable for practical use.

A "ferroelectric liquid crystal material" as used herein is a liquid crystal material which exhibits ferroelectric properties as follows. When an electric field is applied to a dielectric liquid crystal having permanent dipoles, the dipoles are oriented with the direction of the applied electric field and dielectric polarization occurs. When electrostatic interaction between permanent dipoles is strong, the dipoles are arranged in parallel even without application of the external electric field. When dipoles are arranged in parallel, spontaneous polarization exists. The property that the direction of this spontaneous polarization can be reversed by externally applying an electric field is known as "ferroelectricity", and a liquid crystal material having this property is a "ferroelectric liquid crystal material".

In general, liquid crystal materials having an optically active portion exhibit ferroelectric properties in smectic phases. The molecular arrangement is such that the major axis of the molecules is tilted from the normal axis of the smectic liquid crystal layers. It is highly desirable that the liquid crystal material exhibit a chiral smectic C phase ("SmC*") for practical operation of the liquid crystal material over a relatively low voltage range.

Okano and Kobayashi et al introduced compounds of Schiff series, azoxy series and ester series in their publication entitled "The Liquid Crystal—The Basic Edition", p. 140 (1985) as typical ferroelectric liquid crystal materials. However, the Schiff series, azoxy series and ester series compounds have significant disadvantages including chemical instability, low light resistance, high viscosity and the like. Accordingly, at the present time there are a limited number of ferroelectric liquid crystal materials that are suitable for practical use.

When a ferroelectric liquid crystal material is to be used as the electro-optical element in a liquid crystal display cell, some of the properties including temperature range and other electro-optical properties can be adjusted by mixing the material with other types of ferroelectric liquid crystal materials or with non-ferroelectric liquid crystal materials having the desired properties. However, such techniques are not always entirely suitable.

Accordingly, it is desirable to provide an improved ferroelectric liquid crystal material.

SUMMARY OF THE INVENTION

Generally speaking, in accordance with the invention, novel 2-phenylpyridine derivatives are provided. The 2-phenylpyridines are represented by the following formula:

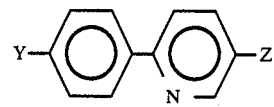

wherein Y is

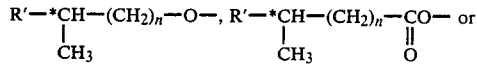

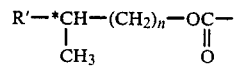

and Z is a straight chain alkyl group having from 1 to 16 carbon atoms,

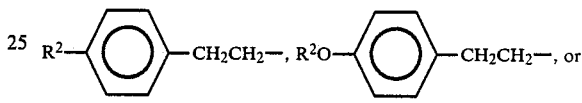

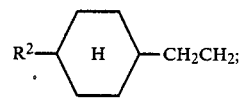

R' is a straight chain alkyl group having from 2 to 12 carbon atoms, $R^2$ is a straight chain alkyl group having from 1 to 12 carbon atoms, n is an integer from 1 to 10 and * is an asymmetric carbon.

Such compounds exhibit ferroelectric properties over a wide temperature range, are stable, have low viscosity and excellent electro-optical response properties. When added to ferroelectric liquid crystal materials they broaden the temperature range within which the ferroelectric properties are exhibited.

Accordingly, it is an object of the invention to provide an improved ferroelectric liquid crystal material.

Another object of the invention is to provide novel 2-phenylpyridine derivatives.

A further object of the invention is to provide novel 2-phenylpyridine derivatives that are useful to add to ferroelectric liquid crystal materials in order to improve the electro-optical properties of the composition.

Yet another object of the invention is to provide a ferroelectric liquid crystal composition including the novel 2-phenylpyridine derivatives.

Yet a further object of the invention is to provide improved ferroelectric liquid crystal compositions that are suitable for practical use.

Still other objects and advantages of the invention will in part be obvious and will in part be apparent from the specification.

The invention accordingly comprises a composition of matter possessing the characteristics, properties, and the relation of components which will be exemplified in the composition hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a phase diagram of

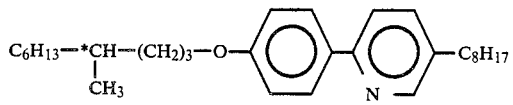

mixed with a conventional ferroelectric liquid crystal material; and

Figure 2:
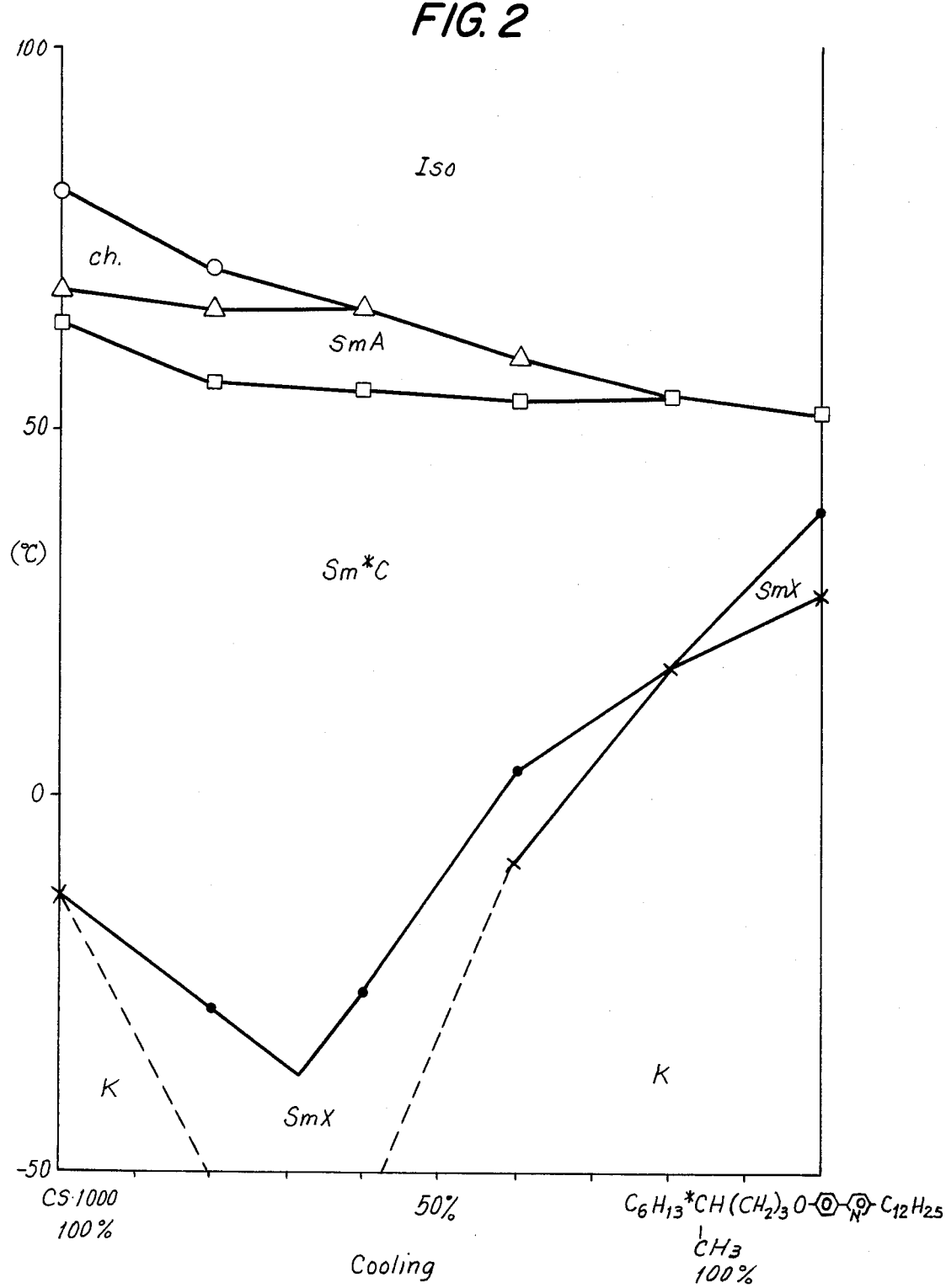

FIG. 2 is a phase diagram of

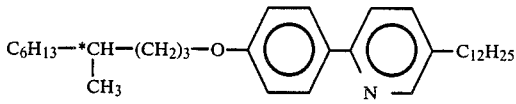

mixed with a conventional ferroelectric liquid crystal material.

DETAILED DESCRIPTION OF THE PREFERRED EMBODIMENTS 2-phenylpyridine derivatives prepared in accordance with the invention have the general formula:

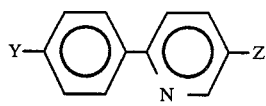

wherein Y is

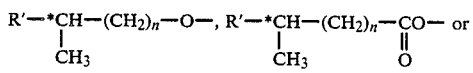

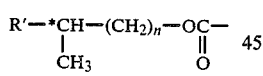

and Z is a straight chain alkyl group having from 1 to 16 carbon atoms,

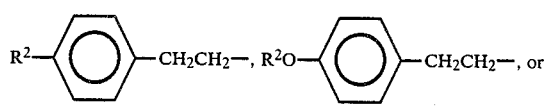

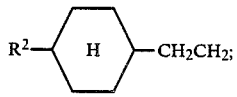

R' is a straight chain alkyl group having from 2 to 12 carbon atoms, R² is a straight chain alkyl group having from 1 to 12 carbon atoms, n is an integer from 1 to 10 and * is an asymmetric carbon.

The 2-phenylpyridine compounds represented by formula (1) can be prepared according to the following reaction scheme:

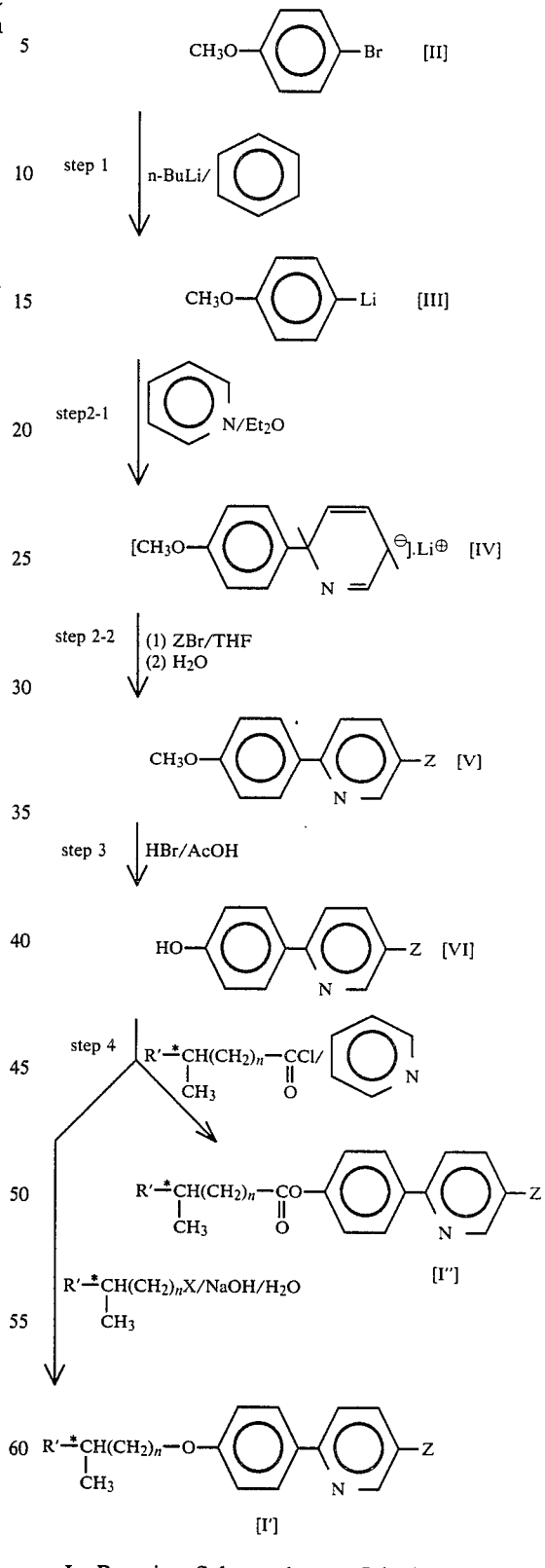

In Reaction Scheme 1, step I includes reacting p-bromoanisole [II] with n-butyllithium in dry benzene to obtain p-methoxyphenyllithium [III]. The resulting compound [III] is reacted with dry pyridine in dry diethyl ether to obtain intermediate compound [IV]. The resulting intermediate compound [IV] dissolved in the reaction solution is reacted with a 1-bromoalkane, 2-(p-alkylphenyl)ethylbromide, 2-(p-alkoxyphenyl)ethylbromide, or 2-(trans-4-alkylcyclohexyl)ethylbromide represented by ZBr in the scheme separately in dry tetrahydrofuran and the resulting solution is hydrolyzed to obtain 2-(p-methoxyphenyl)pyridine-5-yl [V]. Compound [V] is heated with hydrobromic acid in acetic acid to yield 2-(p-hydroxyphenyl)pyridine-5-yl [VI]. The compound [VI] is etherified with an alkylation reagent, such as an optically active halogenated alkyl, sulfonic acidalkylester and the like by a known method to obtain the 2-phenylpyridine ether compound represented by the following formula [I']

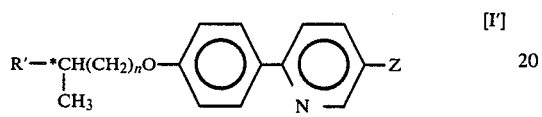
[I']

Alternatively, in step 4 compound [VI] can be esterified with an optically active alkanoyl chloride to obtain the 2-phenylpyridine ester compound represented by the following formula [I"]:

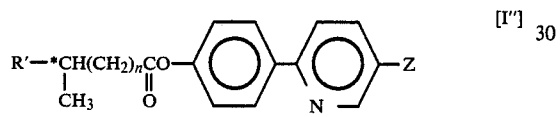
[I"]

A second Reaction Scheme includes the following steps:

<Reaction Scheme II>

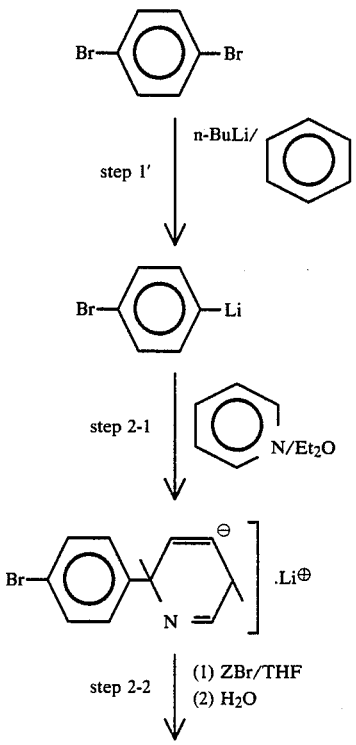

-continued
<Reaction Scheme II>

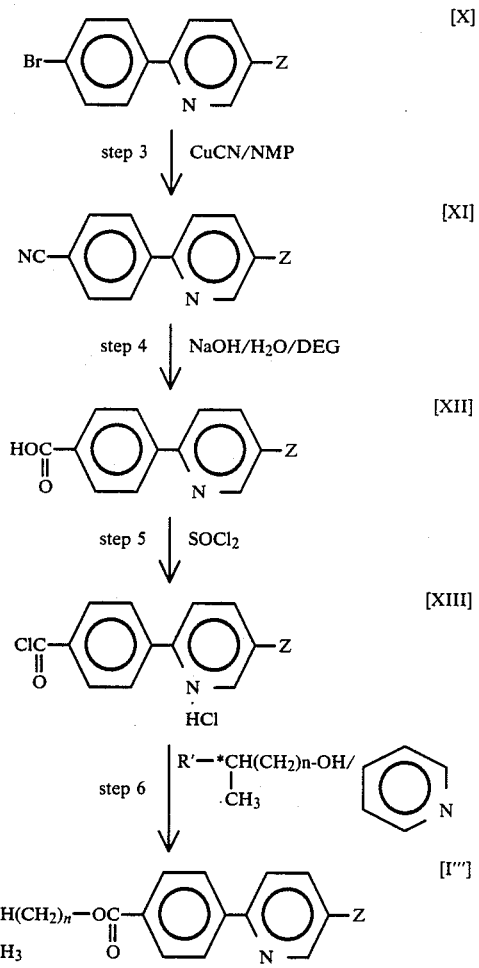

wherein Z is a straight chain alkyl group having from 1 to 16 carbon atoms,

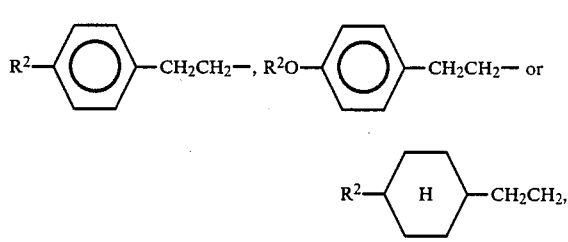

$R^2$ is a straight chain alkyl group having from 1 to 12 carbon atoms, R' is a straight chain alkyl group having from 2 to 12 carbon atoms, n is an integer from 1 to 10, * is an asymmetric carbon and X is halogen or sulfonate ester residue.

In Reaction Scheme II, 1,4-dibromobenzene [VII] is reacted with n-butyllithium in dry benzene to obtain p-bromophenyllithium [VIII]. Compound [VIII] is reacted with dry pyridine in dry diethylether to obtain intermediate compound [IX]. The resulting intermediate compound [IX] dissolved in the reaction solution is reacted with 1-bromoalkane, 2-(p-alkylphenyl)ethylbromide, 2-(p-alkoxyphenyl)ethylbromide or 2-(trans-4-alkylcyclohexyl)ethylbromide represented by ZBr in the scheme separately in dry tetrahydrofuran and the resulting solution is hydrolyzed to obtain 2-(p-bromophenyl)pyridine-5-yl [X]. Compound [X] is reacted with copper (I) cyanide in N-methylpyrrolidone to obtain 2-(p-cyanodiphenyl)pyridine-5-yl [XI]. Compound [XI], sodium hydroxide and water are boiled in ethylene glycol to carry out the hydrolysis and obtain p-(pyridine-2,5-diyl)benzoic acid [XII]. Compound [XII] is reacted with thionyl chloride to obtain p-(pyridine-2,5-diyl)benzoic acid chloride [XIII]. As the final step, compound [XIII] is esterified with an optically active alcohol by a known method to obtain the compound [I'''].

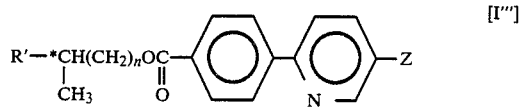

Preparation of 2-phenylpyridine derivatives in accordance with the invention are shown in the following examples. These examples are presented for purposes of illustration and are not intended to be construed in a limiting sense.

EXAMPLE 1

Preparation of (R)-2-[p-(4-methyldecyloxy)phenyl]-5-octylpyridine 1. 18.7 g (0.1 mol) of p-bromoanisole was dissolved in 70 ml of dry benzene in a stream of nitrogen. 74 ml (0.12 mol) of a 15% solution of n-butyllithium in hexane was added dropwise to the p-bromoanisole solution with stirring and stirring was maintained for 12 hours at room temperature. The reaction produced a precipitate of p-methoxyphenyllithium that was filtered in a stream of nitrogen, washed with dry hexane and dried in vacuum.

2-1. The product was dissolved in 150 ml of dry diethyl ether and chilled to a temperature of 5° C. or lower on an ice bath. 6.3 g (0.08 mol) of dry pyridine was added dropwise with stirring and stirring was maintained for an additional 3 hours at room temperature.

2-2. The reaction solution was chilled to a temperature of about −15° C. or less on a freezing mixture while 80 ml of dry tetrahydrofuran was added dropwise. 40 ml of tetrahydrofuran containing 15.4 g (0.08 mol) of octylbromide was dropwise added to the resulting solution. The temperature of the solution was raised to room temperature and stirring was maintained for 1 hour.

100 ml of water was added to the reaction solution. The ether layer was separated and washed three times with water. Ether was removed by distillation. The residue was chromatographed over 5.0φ×100 (cm) of silica gel and developed with hexane followed by benzene. The effluent was recrystallized from a mixture of methanol and acetone to yield 10.8 g (0.036 mol) of 2-(p-methoxyphenyl)-5-octylpyridine.

3. The 2-(p-methoxyphenyl)-5-octylpyridine was dissolved in 100 ml of acetic acid. 8 ml of 48% hydrobromic acid was added to the reaction solution and the solution was heated for 15 hours under reflux. 100 ml of water was added to the reaction solution and the organic layer was extracted with chloroform. After washing the extract three times with water, the chloroform was removed by distillation. The residue was recrystallized from a mixture of acetone and hexane to yield 8.3 g (0.029 mol) of 2-(p-hydroxyphenyl)-5-octylpyridine.

4. 20 ml of a 30% aqueous solution of sodium hydroxide was added dropwise to a mixture of 2 g (0.007 mol) of 2-(p-hydroxyphenyl)-5-octylpyridine and 1.65 g (0.007 mol) of (R)-1-bromo-(4-methyl)decane with stirring. The resulting solution was heated to a temperature between about 90° and 100° C. for 3 hours. 150 ml of water was added to the reaction solution and the organic layer was extracted with chloroform. After washing the extract three times with water, chloroform was removed by distillation. The residue was chromatographed over 2.5×100 (cm) of silica gel and developed with hexane and benzene. The effluent was repeatedly recrystallized from a mixture of methanol and acetone to yield 1.44 g (0.0033 mol) of (R)2-[p-(4-methyldecyloxy)phenyl]-5-octylpyridine.

EXAMPLES 2–22

The procedures of Example 1 were followed to prepare the 2-phenylpyridine derivatives identified as Embodiments in the following Table 1.

EXAMPLE 23

Preparation of (S)-2-[p-(4-methyldodecyloxy)phenyl]-5-[2-(p-pentyloxyphenyl)ethyl]pyridine (S)-p-(4-methyldodecyloxy)bromobenzene was used as the starting material in place of the p-bromobenzene of Example 1. Steps 1 to 2-2 of Reaction Scheme I were followed to yield the (S)-2-(4-methyldodecyloxy)phenyl-5-2-(p-pentyloxyphenyl)ether pyridine.

1. 100 g (0.282 mol) of S-p-(4-methyldodecyloxy)bromobenzene was dissolved in 100 ml of dry benzene in a stream of nitrogen. 174 ml (0.282 mol) of a 15% solution of n-butyllithium in hexane was dropwise added to the solution with stirring and stirring was maintained for 12 hours at room temperature. The reaction produced a precipitate of (S)-p-(4-methyldodecyloxy)phenyllithium that was filtered, washed with dry hexane and dried in vacuum.

2-1. The product was dissolved in 330 ml of dry diethyl ether in a stream of nitrogen. 110 g of the resulting solution was chilled to a temperature of 5° C. or lower on an ice bath. 7.9 g (0.1 mol) of dry pyridine was dropwise added with stirring and stirring was maintained for 3 hours at room temperature.

2-2. The reaction solution was chilled to a temperature of −10° C. or lower on a freezing mixture while 70 ml of dry tetrahydrofuran was added dropwise. 50 ml of tetrahydrofuran solution containing 27.1 g (0.1 mol) of 2-(p-pentyloxyphenyl)ethylbromide was added dropwise to the resulting solution with stirring and stirring was continued for 1 hour at room temperature. 150 ml of water was added to the reaction solution and the ether layer was extracted. After washing the extract three times with water, the ether was removed by distillation. The residue was repeatedly recrystallized from a mixture of methanol and acetone to yield 7.0 g of (S)-2-[p-(4-methyldodecyloxy)phenyl]-5-[2-(p-pentyloxyphenyl)ethyl]pyridine.

EXAMPLE 24

Preparation of
(S)-2-[p-(4-methyldecyloxy)phenyl]-5-[2-(trans-4-butyl-cyclohexyl)ethyl]pyridine 1. 110 g (0.336 mol) of p-(4-methyldecyloxy)bromobenzene was dissolved in 119 ml of dry benzene in a stream of nitrogen. 247 ml (0.4 mol) of a 15% solution of n-butylithium in hexane was dropwise added to the solution with stirring and stirring was maintained for 12 hours at room temperature. After completion of the reaction, a precipitate of (S)-p-(4-methyldecyloxy)-phenyllithium was produced and filtered. The precipitate was washed with dry hexane and the resulting sample was dried in vacuum.

2-1. The product was dissolved in 360 ml of dry diethyl ether in a stream of nitrogen. 120 ml of the resulting solution was chilled to a temperature of 5° C. or less on an ice bath. 10 g (0.127 mol) of dry pyridine was dropwise added to the resulting solution with stirring and stirring was maintained for 3 hours at room temperature.

2-2. The reaction solution was chilled to a temperature of −10° C. or lower on a freezing mixture while 80 ml of dry tetrahydrofuran was dropwise added. Then 50 ml of a tetrahydrofuran solution containing 30 g (0.12 mol) of 2-(trans-4-butylcyclohexyl)ethylbromide was dropwise added to the resulting solution with stirring and the solution was stirred for 1 hour at room temperature.

150 ml of water was added and the ether layer was extracted. After washing the extract three times with water, ether was removed by distillation. The residue was repeatedly recrystallized from a mixture of methanol and acetone to yield 5.6 g of (S)-2-[p-(4-methyldecyloxy)phenyl]-5-[2-(trans-4-butylcyclohexyl)ethyl]-pyridine.

EXAMPLE 25

1.0 g (0.0035 mol) of 2-(p-hydroxyphenyl)-5-octylpyridine obtained in Step 1 as described in Example 1, 0.6 g (0.0035 mol) of (S)-4-methylhexylcarbonylchloride and 12 ml of pyridine were heated to 60° C. for 12 hours. The reaction solution was poured into a mixture of 14 ml of hydrochloric acid and 28 g of ice and the organic layer was extracted with chloroform. After washing the extract with a 10% aqueous solution of potassium hydroxide once and then three times with water, chloroform was removed by distillation. The residue was chromatographed over silica gel and the effluent was recrystallized from a mixture of methanol and acetone to yield 0.35 g of 2-[4-(S-methylhexylcarbonyloxy)phenyl]-5-octylpyridine.

EXAMPLE 26

Preparation of
2-[4-(S-2-methylbutoxycarbonyl)phenyl]-5-octylpyridine 1. 878 g (3.72 mol) of 1,4-dibromobenzene was dissolved in 1.8 g of dry benzene in a stream of nitrogen. 2 l (3.24 mol) of a 15% solution of n-butyllithium in hexane was added dropwise to the resulting solution and the solution was stirred for 12 hours at room temperature. The precipitate of 4-bromophenyllithium was filtered in a stream of nitrogen, washed with dry hexane and dried in vacuum.

2-1. The product was dissolved in 1.5 l of dry diethyl ether and chilled to a temperature of 5° C. or less on an ice bath. 212 g (2.68 mol) of dry pyridine was added dropwise with stirring and stirring was maintained for 3 hours at room temperature.

2-2. The reaction solution was chilled to a temperature of −60° C. or less while 5.6 of dry tetrahydrofuran was added dropwise. 486 g (2.52 mol) of 1-bromooctane was added dropwise to the resulting solution. The solution temperature was raised to room temperature and stirring was maintained for 1 hour.

1 l of water was added to the reaction solution. The ether layer was extracted and washed with water 3 times and then the ether was removed by distillation. The residue was distilled under reduced pressure (130° to 142° C./2 mmHg) and was recrystallized from methanol to obtain 47.6 g (0.138 mol) of 2-(p-bromophenyl)-5-octylpyridine.

3. 94 ml of N-methylpyrrolidone was added to the 47.6 g (0.138 mol) of the 2-(p-bromophenyl)-5-octylpyridine. Then 19.3 g (0.216 mol) of copper (I) cyanide was added and the solution was refluxed for 2 hours. A mixture of 69 g of iron (II) chloride, 13.8 ml of concentrated hydrochloric acid and 69 ml of water was added to the mixture solution and the organic layer was extracted with chloroform. The extract was washed with a 10% aqueous solution of potassium hydroxide and then three times with water. Chloroform was removed by distillation. The residue was distilled under reduced pressure (210° to 220° C./2 mmHg) and recrystallized from methanol to obtain 33 g (0.1113 mol) of 2-(p-cyanophenyl)-5-octylpyridine.

4. 33 g of the resulting of 2-(p-cyanophenyl)-5-octylpyridine was mixed with 22.6 g of sodium hydroxide, 565 ml of ethylene glycol and 20.3 ml of water and was maintained under reflux for 6 hours. The reaction solution was poured into a mixture of 73 ml of concentrated hydrochloric acid and 148 g of ice and the precipitate was filtered and washed with water. The product was recrystallized from ethanol to obtain 30 g (0.102 mol) of p-(5-octylpyridyl)benzoic acid.

5. 30 g (0.102 mol) of the resulting p-(5-octylpyridyl)-benzoic acid was added to 24.3 g (0.204 mol) of thionyl chloride and reflux was maintained for 5 hours. The surplus thionyl chloride was removed by distillation and the product was recrystallized from hexane to obtain 34.5 g (0.0986 mol) of p-(5-octylpyridyl)benzoylchloride hydrochloride.

6. 4 g (0.0114 mol) of the resulting p-(5-octylpyridyl)-benzoylchloride hydrochloride and 1.2 g (0.0137 mol) of (S)-1-bromo-2-methylbutanol were added to 23.5 ml of pyridine and the resulting solution was heated for 4 hours at 90° C.

The reaction solution was added to a mixture of 43.5 ml of concentrated hydrochloric acid and 87 g of ice and the organic layer was extracted with chloroform. The organic layer was washed with once with 10% potassium hydroxide and then three times with water. Chloroform was removed by distillation and the residue was chromatographed over silica gel and developed with chloroform. The effluent was recrystallized from a mixture solvent of methanol and acetone to obtain 0.8 g (0.0021 mol) of S-2-[p-(2-methylbutoxy-carbonyl)-phenyl]-5-octylpyridine.

EXAMPLES 27 AND 28

Compounds 27 and 28 in Table 1 were prepared by the method shown in Example 1.

TABLE 1

| Embodiments | R¹ | Z | n | K | SmX | SmY* | SmC* | SmA | Ch | Iso |
|---|---|---|---|---|---|---|---|---|---|---|
| | \*R¹CH(CH₂)ₙO—〈ph〉—〈pyN〉—Z with CH₃ | | | | | | | | | |
| 2 | $C_2H_5$ | $C_6H_{13}$ | 1 | · 50.2 (20.5·) | — | — | — | — | — | · |
| 3 | $C_2H_5$ | $C_8H_{17}$ | 1 | · 48.1 (23.5·) | — | — | — | — | — | · |
| 4 | $C_2H_5$ | $C_9H_{19}$ | 1 | 18.9· (−25·) | 58.9 | — | — | (44.0·) | — | · |
| 5 | $C_2H_5$ | $C_8H_{17}$ | 3 | 32.6· (−7.4·) | 50.7 | (31.8·) | (60.3·) | 63.0 — | — | · |
| 6 | $C_2H_5$ | $C_9H_{19}$ | 3 | 41.4· (5.2·) | 53.4 | (51.8·) | (63.3·) | 68.0 — | — | · |
| 7 | $C_3H_7$ | $C_9H_{19}$ | 3 | 42.3· (33.8·) | 58.0 — | (47.7·) | (60.5·) | 64.4— | — | · |
| 8 | $C_3H_7$ | $C_{11}H_{23}$ | 3 | 36.2· (20.5·) | 55.6 | (43.0·) | (52.6·) | 58.7 — | — | · |
| 9 | $C_4H_9$ | $C_{10}H_{21}$ | 3 | · 66.2 (33.5·) | (40.5·) | — | (57.2·) | — | — | · |
| 10 | $C_5H_{11}$ | $C_8H_{17}$ | 3 | · 35.0· (11.6·) | 47.1 — (46.5·) | | (58.5·) | 62.4 — | — | · |
| 11 | $C_5H_{11}$ | $C_9H_{19}$ | 3 | · 26.6· (0.4·) | 39.9 — (39.0·) | | (54.6·) | 55.1 — | — | · |
| 12 | $C_5H_{11}$ | $C_{10}H_{21}$ | 3 | · 35.3· (−2.7·) | 54.7 — | | (36.4·) | — | — | · |
| 1 | $C_6H_{13}$ | $C_8H_{17}$ | 3 | · 50.0 (−15.4·) | (4.1·) | | (46.8·) | — | — | · |
| 13 | $C_6H_{13}$ | $C_{12}H_{25}$ | 3 | · 50.7· (28.0·) | 54.8 — (38.6·) | | (51.7·) | — | — | · |
| 14 | $C_8H_{17}$ | $C_8H_{17}$ | 3 | · 48.2 (−6.6·) | (27.3·) | | (43.3·) | — | — | · |
| 15 | $C_8H_{17}$ | $C_9H_{19}$ | 3 | · 42.2· (−1.4·) | 50.1 — (34.5·) | | (48.4·) | — | — | · |
| 16 | $C_8H_{17}$ | $C_{12}H_{25}$ | 3 | · 45.0· (38.0·) | 59.0 — (58.5·) | | (70.6·) · 56.0 | 71.5 — | — | · |
| 17 | $C_3H_7$ | $C_7H_{15}$ | 5 | · 30.5 ·42.5 (0.2·) | (36.3·) | | (53.2·) | — | — | · |
| 18 | $C_3H_7$ | $C_9H_{19}$ | 5 | ·33.0 (8.1·) | ·52.2 (51.9·) | — | ·68.1 | — | — | · |
| 19 | $C_3H_7$ | $C_{11}H_{23}$ | 5 | ·28.4 (−4.0·) | ·65 (17.5·) | (36.8·) | (47.0·) | — | — | · |
| 20 | $C_4H_9$ | $C_7H_{15}$ | 5 | ·43.4 (28.6·) | ·59.8 | (50.5·) | ·73.5 (73.0·) | — | — | · |
| 21 | $C_4H_9$ | $C_9H_{19}$ | 5 | ·37.2 (12.0·) | ·56.8 (51.4·) | | ·63.7 (60.4·) | — | — | · |
| 22 | $C_4H_9$ | $C_{11}H_{23}$ | 5 | ·26.6 (11.5·) | ·45.1 (32.0·) | — | ·58.9 (54.7·) | ·71.2 (68.7·) | — | · |
| 23 | $C_8H_{17}$ |  $C_5H_{11}O$—〈ph〉— | 3 | ·40.0 | | — | | | — | 131.8· |
| | —CH₂CH₂— | | | (−13·) | (81.0·) | | (103·) | (120.1·) | | |

TABLE 1-continued

| Embodiments | R¹ | Z | n | Phase transition temperature (°C.) | | | | | |
|---|---|---|---|---|---|---|---|---|---|
| | | | | K | SmX | SmY* | SmC* | SmA | Ch | Iso |
| 24 | $C_8H_{17}$ | 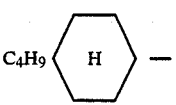 | 3 | · −23.0 | — | — | — | ·120.5 | — | · |

$$R^{1*}CH(CH_2)_nCO-\text{[biphenyl-pyridine]}-Z$$
$$\quad\quad |\quad\quad\quad ||$$
$$\quad CH_3\quad\quad O$$

| 25 | $C_2H_5$ | $C_{10}H_{21}$ | 3 | ·46.5 (35.0·) | ·52.7 (44.9·) | — | — | — | — | · |

$$R^{1*}CH(CH_2)_nOC-\text{[biphenyl-pyridine]}-Z$$
$$\quad\quad |\quad\quad\quad ||$$
$$\quad CH_3\quad\quad O$$

| 26 | $C_2H_5$ | $C_8H_{17}$ | 1 | ·27.2 (22.4) | — | — | — | — | — | · |
| 27 | $C_4H_9$ | $C_8H_{17}$ | 3 | · 0.5 (−27.2·) | — | — | (78.0·) | ·27.2 | — | · |
| 28 | $C_5H_{11}$ | $C_8H_{17}$ | 3 | · 7.0 (−28.6·) | — | — | (−2.0·) | ·24.2 | — | · |

In Table 1, K represents the crystalline phase, SmX the unidentified smectic phase, SmY* the electric field responsive unidentified smectic phase, SmA the smectic A phase, Ch the cholesteric phase and I the anistropic liquid crystal phase. The figure in parentheses refers to the monotropic phase transition temperature. A differential scanning calorimeter was used to measure the phase transition temperature and to confirm the number of mesophases. The texture was observed with a polarized microscope equipped with a Metteler FP82 heating stage and FP80 temperature controller unit.

As shown in Table 1, most of the compounds represented by formula (1) present the ferroelectric liquid crystal phases SmC* and SmY*. The ferroelectric liquid crystal phases appear over a low temperature range, room temperature range and high temperature range. Accordingly, the ferroelectric liquid crystal temperature range extends from 0° C. and lower to 100° C. and higher.

The ferroelectric liquid crystal materials have several sequences of phase transitions including Iso-SmA-SmC*, Iso-Ch-SmA-SmC* or Iso-SmC*. Compounds which transform directly from Iso to SmC* are particularly effective for expanding the temperature range of ferroelectric liquid crystal phases when mixed with other compounds. Significantly, the compounds of formula (1) are excellent in that the liquid crystal material itself exhibits the ferroelectric properties. Some of the compounds represented by formula (1) are restricted in exhibiting ferroelectric properties by the arrangement of the permanent dipole at the molecular level, by the substitution of short chain alkyl groups and the like. Notwithstanding that some of the compounds of formula (I) do not present ferroelectric properties, such compounds exhibit stable smectic phases as a single compound over an expansive temperature range extending up to about 100° C. Materials substituted with short chain alkyl groups exhibit low viscosity. Furthermore, since the basic skeleton of compounds that do not have ferroelectric properties is a chiral structure similar to a ferroelectric liquid crystal material, these compounds are excellent with respect to mutual solubility with ferroelectric liquid crystal materials or with other known ferroelectric liquid crystal series. These compounds can be mixed appropriately so that thermal stability of the ferroelectric liquid crystal phase is obtained and the viscosity is reduced.

Compounds represented by formula (1) do not deteriorate when subjected to environmental factors such as heat, temperature, atmosphere, electro-magnetic radiation within the range of infrared rays, visible rays, ultraviolet rays, electric fields and the like. The compounds thus present remarkable stability. Moreover, the pyridine ring induces the same intermolecular effect as an intermolecular interaction of the type discussed in Japan Display '83, SID, p. 224 and introduced by B. S. Scheuble et al. Accordingly, various electro-optical properties are expected to be enhanced.

APPLICATION EXAMPLE 1

The chiral smectic liquid crystal compound prepared in Example 1 having the formula

Figure 1:
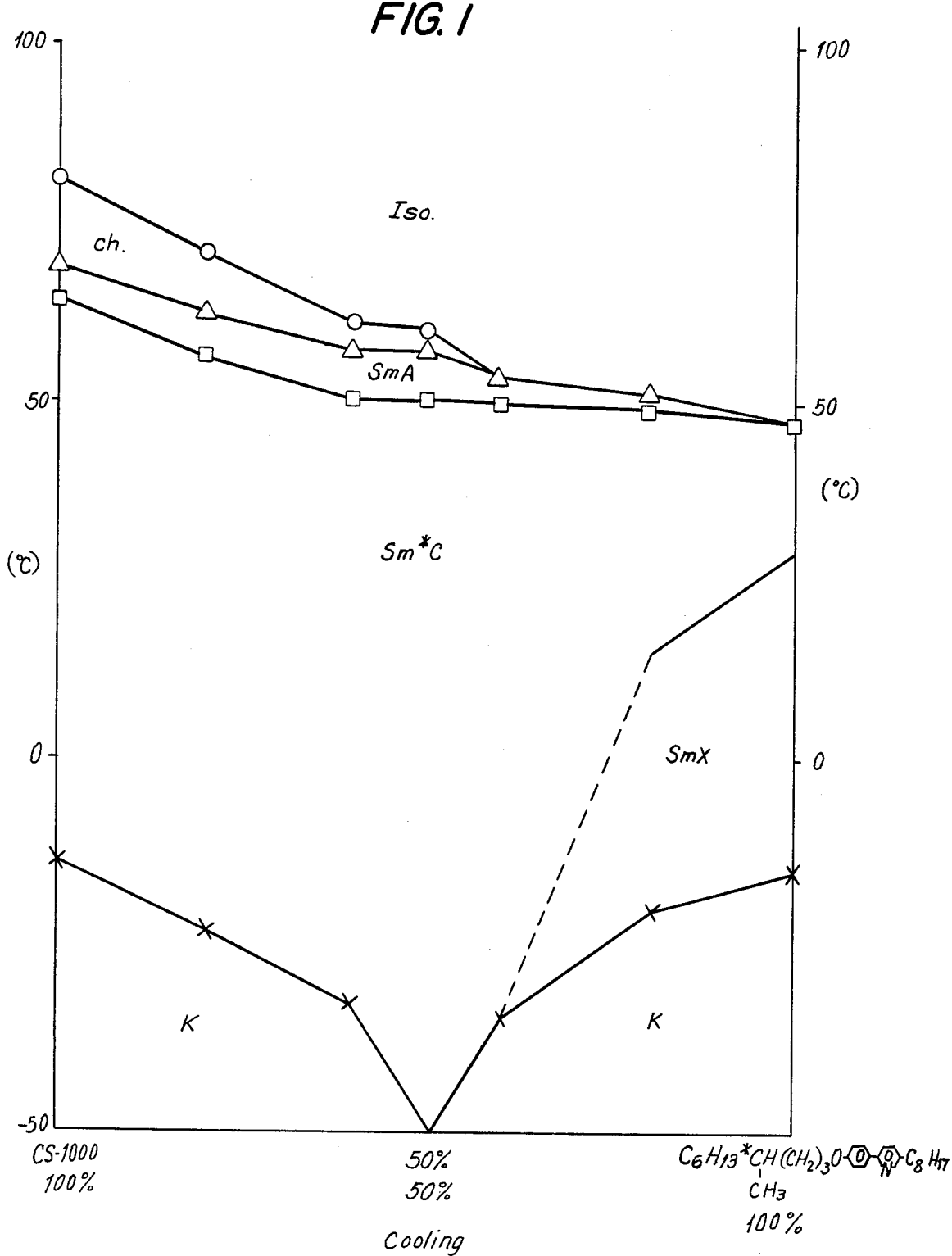

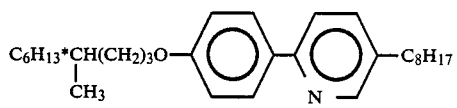

does not have a liquid crystal phase at temperatures above the SmC* phase as shown in FIG. 1. When mixed with a ferroelectric liquid crystal composition CS-1000 manufactured by Chisso Corporation in the proportions shown in FIG. 1, the temperature of the SmA declined to that of the SmC* transition point as the amount of the 2-phenylpyridine was increased. Upon increasing the addition of 2-phenylpyridine, the lower temperature of the lower transition point of SmC* phase declined significantly. Accordingly, the total SmC* phase expanded.

When

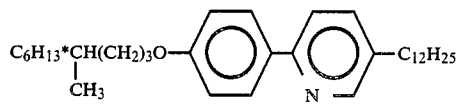

(Embodiment 13) was added to the CS-1000 as shown in FIG. 2, the SmC* phase also expanded in a similar manner as described.

APPLICATION EXAMPLE 2

A liquid crystal composition shown in Table 2 was thermally sealed between two glass substrates having transparent electrodes which had rubbed surfaces and assembled to form a liquid crystal cell having a thickness of the cell between about 1 to 2 μm. The resulting electro-optical element was inserted between 2 polarizers with the axis of polarization crossed at right angles to each other. When ±12 V of alternating current was applied to the electro-optical element, it responded according to the direction of the electric field.

TABLE 2

| Components | Composition (weight %) |
|---|---|
| CS-1000 (ferroelectric liquid crystal composition made by Chisso Corporation) CS-1000 | 70 |
| $C_6H_{13}$*CH(CH$_2$)$_3$O—〈phenyl〉—〈pyridyl〉—$C_{12}H_{25}$ (with CH$_3$ branch) | 20 |
| $C_8H_{17}$—〈phenyl〉—〈phenyl〉—COO—〈phenyl〉—CH$_2$*CHC$_2$H$_5$ (with CH$_3$ branch) | 10 |

| phase transition point (C) | SmO* | | SmA | | Ch | | Iso |
|---|---|---|---|---|---|---|---|
| | | 58 | | 71 | | 7.7 | |

The SmA/SmC* transition point of the composition of Table 2 occurred at a comparatively high temperature, specifically 58° C. A wide SmC* phase temperature range was also obtained. MR (mesophase range) was near room temperature (25° C.) and was acceptable, specifically 10° C. The contrast maintained a desirable ratio of 1:10 within the temperature range. The ratio of light transmission Ip when the electric field was applied to light transmission Im when the electric field was removed (at the time of memory) was Im/Ip 0.9. The memory properties were also satisfactory.

Accordingly, the 2-phenylpyridine derivatives prepared in accordance with the invention have numerous advantageous properties. Specifically, the 2-phenylpyridine derivatives show ferroelectric properties over an extremely wide temperature range, are stable and have strong intermolecular interaction. In addition, the properties of 2-phenylpyridine derivatives can be adjusted according to the desired use. Such adjustable thermal properties include properties of the liquid crystals, electro-optical properties and the like. Adjustment can be accomplished by mixing the 2-phenylpyridine derivatives with each other or with other ferroelectric liquid crystal series. Accordingly, improved ferroelectric liquid crystal compositions suitable for practical use are obtained.

It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. 2-phenylpyridine derivatives represented by the general formula:

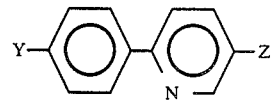

wherein Y is

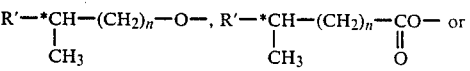

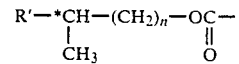

and Z is a straight chain alkyl group having from 1 to 16 carbon atoms,

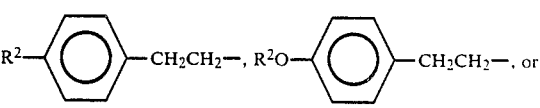

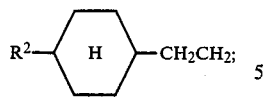

R' is a straight chain alkyl group having from 2 to 12 carbon atoms, R² is a straight chain alkyl group having from 1 to 12 carbon atoms, n is an integer from 1 to 10 and * is an asymmetric carbon.

2. The 2-phenylpyridine derivative of claim 1, wherein Y is

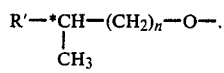

3. The 2-phenylpyridine derivative of claim 2, wherein R' is a straight chain alkyl group having from 2 to 8 carbon atoms, Z is a straight chain alkyl group having from 6 to 12 carbon atoms and n is an integer from 1 to 5.

4. The 2-phenylpyridine derivative of claim 2, wherein Z is

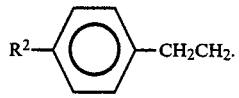

5. The 2-phenylpyridine derivative of claim 2, wherein Z is

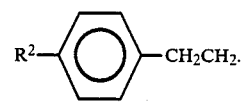

6. The 2-phenylpyridine derivative of claim 1, wherein Y is

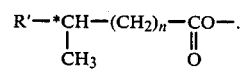

7. The 2-phenylpyridine derivative of claim 6, wherein R¹ is a straight chain alkyl group having from 6 to 12 carbon atoms, Z is a straight chain alkyl group having from 6 to 12 carbon atoms and n is an integer from 1 to 5.

8. The 2-phenylpyridine derivative of claim 1, wherein Y is

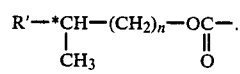

9. The 2-phenylpyridine derivative of claim 8, wherein R¹ is a straight chain alkyl group having from 2 to 8 carbon atoms, Z is a stragith chain alkyl group having from 6 to 12 carbon atoms and n is an integer from 1 to 5.

* * * * *